US 6,617,111 B2

(12) United States Patent
Nellis et al.

(10) Patent No.: US 6,617,111 B2
(45) Date of Patent: Sep. 9, 2003

(54) METHOD FOR MEASURING UNIT ACTIVITY OF AN ENZYME

(75) Inventors: David F Nellis, Frederick, MD (US); Stephanie Nilsen, Frederick, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/852,093

(22) Filed: May 10, 2001

(65) Prior Publication Data

US 2003/0003598 A1 Jan. 2, 2003

(51) Int. Cl.[7] ............................ C12Q 1/68; C12P 19/34; G01N 33/00; B01D 57/02; C07H 21/02
(52) U.S. Cl. ............................ 435/6; 435/91.1; 436/94; 204/450; 204/456; 536/23.1
(58) Field of Search ............................ 435/6, 91.1, 183; 436/94; 536/23.1; 204/450, 451, 456

(56) References Cited

U.S. PATENT DOCUMENTS 6,131,072 A    10/2000    Holden et al. ................ 702/20

OTHER PUBLICATIONS

Aultman, K., et al., Partial P1 Nuclease Digestion as a Probe of tRNA Structure, Eur. J. Biochem. 124, pp. 471–476, Nov. 1981.*

Romy Kandzia, et al, Purificationa and characterization of lanatoside 15'–O–acetylesterase from Digitalis Ianata Ehrh, Planta (1998) 204: pp. 383–389.*

Kettling Ulrich et al., "Real–Time Enzyme Kinetics Monitored by Dual–Color Fluorescence Cross–Correlation Spectroscopy," Biochemistry, vol. 95, Issue 4, Feb. 17, 1998, pp. 1416–1420, http://www.pnas.org/cgi/content/full, 12 pages.

Press William H. et al., "Numerical Recipes in C: The Art of Scientific Computing," Second Edition, Cambridge University Press, 1988–1992, Chapter 10, pp. 394–455.

(List continued on next page.)

*Primary Examiner*—Ethan Whisenant
*Assistant Examiner*—Frank Wei Min Lu
(74) *Attorney, Agent, or Firm*—Sterne, Kessler, Goldstein & Fox, P.L.L.C.

(57) ABSTRACT

A system, method and computer program product is provided for processing images of an electrophoretic separation medium to determine the unit activity of an enzyme. A test aliquot, comprising a macromolecule (such as, DNA, RNA, protein, peptide or the like) and diluted enzyme concentration, is distributed in the separation medium. The enzyme concentration acts as a catalysis to cleave the macromolecule into distinct fragments during electrophoresis. A set of intensity data profiles are produced from images of the fragments. The profiles are stacked and vertically aligned to designate and assign the fragments to their respective lanes. A group of partial bands and final bands are selected from the fragments. Peak integrations are implemented to measure the intensity of the partial and final bands. A series of intensity ratios are computed from the peak integrations. The intensity ratios are normalized and plotted to produce a trend. A threshold crossing value is derived from the effective dilution factor corresponding to a point at which the trend crosses a threshold crossing level. The threshold crossing value is used to determine a calibration factor. The calibration factor used to determine a reported unit call.

12 Claims, 8 Drawing Sheets

OTHER PUBLICATIONS

Press William H. et al., "Numerical Recipes in C: The Art of Scientific Computing," Second Edition, Cambridge University Press, 1988–1992, Chapter 15, pp. 656–706.

Karlovsky P., "Calculation of Individual Cleavage Rates from Partial Digests in Restriction Endonuclease Kinetics," Journal of Theoretical Biology, vol. 132, No. 1, May 7, 1988, http://www.ncbi.nlm.nih.gov, 1 page. abstract only.

Hinsch B. et al., "Reaction Kinetics of Some Important Site–Specific Endonuclease," Nucleic Acids Res., vol. 9, No. 13, Jul. 10, 1981, http://www.ncbi.nlm.nih.gov, 1 page. abstract only.

Wright David J. et al., "The Kinetic Mechanism of EcoRI Endonuclease," Journal of Biological Chemistry, vol. 274, No. 45, Nov. 5, 1999, pp. 31896–31902, http://www.jbc.org/cgi/content/full/274/45/31896, 17 pages.

Wright David J. et al., "The Kinetic Mechanism of EcoRI Endonuclease*," The Journal of Biological Chemistry, The American Society for Biochemistry and Molecular Biology, Inc., 1999, vol. 274, No. 45, Nov. 5, 1999, pp. 31896–31902.

Koltermann Andre et al., "Rapid assay processing by integration of dual–color fluorescence cross–correlation spectroscopy: High throughput screening for enzyme activity," The National Academy of Sciences, 1998, vol. 95, Feb. 1998, pp. 1421–1426.

Kettling Ulrich et al., "Real–time enzyme kinetics monitored by dual–color fluorescence cross–correlation spectroscopy," The National Academy of Sciences, 1998, vol. 95, Feb. 1998, pp. 1416–1420.

Coleman Hugh W. et al., "Experimentation and Uncertainty Analysis for Engineers: Second Edition," John Wiley & Sons, Inc., 1999, pp. 34–37, 162–164 and 189–191.

Jeltsch A et al., "Kinetic Characterization of Linear Diffusion of the Restriction Endonuclease EcoRV on DNA," Biochemistry, vol. 37, No. 8, Feb. 1998, HealthGate® Data Corp, 1999, http://www.healthgate.com/cgi–bin/g–format.cgi, 2 pages. (abstract only).

Kettling Ulrich et al., "Real–time Enzyme Kinetics monitored by Dual–Color Fluorescence Cross–Correlation Spectroscopy," Biochemistry, vol. 95, Issue 4, Feb. 17, 1998, http://www.pnas.org/cgi/content/abstracts, The National Academy of Sciences, 1998, 2 pages. (abstract) only.

Koltermann Andre et al., "Rapid Assay Processing by Integration of Dual–Color Fluorescence Cross–Correlation Spectroscopy: High Throughput Screening for Enzyme Activity," Biochemistry, vol. 95, Issue 4, Feb. 17, 1998, http://www.pnas.org/cgi/content/abstract, The National Academy of Sciences, 1998, 2 pages. abstract only.

Conlan L H et al., "Modulating Restriction Endonuclease Activities and Specificities Using Neutral Detergents," Biotechniques, vol. 27, No. 5, 1999, http://www.ncbi.nlm.nih.gov, 2 pages. abstract only.

Hensley P. et al., "The Time–Resolved Kinetics of Superhelical DNA Cleavage by B Restriction Endonuclease," Journal of Biological Chemistry, vol. 265, No. 25, Sep. 5, 1990, http://www.ncbi.nlm.nih.gov, 2 pages. abstract only.

* cited by examiner

METHOD FOR MEASURING UNIT ACTIVITY OF AN ENZYME

BACKGROUND OF THE INVENTION

1. Field of the Invention

The present invention relates generally to analyzing an enzyme solution. More particularly, the invention relates to facilitating an activity determination for gel-based/chromatographic-based endpoint or dose response analysis.

2. Related Art

Electrophoresis is a technique used to separate and analyze single charged molecules. The charged molecules can be placed on any type of support matrix, such as paper, cellulose acetate, starch gel, agarose gel, or acrylamide gel. Generally, a buffer is run in a separation medium containing the support matrix, and an electric field is applied to the support matrix. At the end of the run, the support matrix is stained appropriately for visualization of the molecules within the matrix.

Since agarose and acrylamide gels are porous substances, an agarose or acrylamide gel-based separation medium permits the molecules to be separated by size or molecular weights. The gels, therefore, retard or prevent larger molecules from moving, and allow the smaller molecules to migrate freely. Agarose gels are generally used to separate larger macromolecules, such as, nucleic acids, large proteins and protein complexes, because agarose gels tend to be more rigid and easy to handle. Acrylamide gels, on the other hand, are more commonly used to separate medium or smaller-sized proteins and small oligonucleotides requiring a smaller gel pore size for retardation.

Nucleic acids, including deoxyribonucleic acid (DNA) and ribonucleic acid (RNA), tend to carry a negative charge in any buffer used for electrophoresis. As such, nucleic acids have a propensity to separate according to their molecular weight. The electrophoretic separation of a protein, however, is based on its electrical charge and molecular weight. Since proteins are amphoteric compounds, their electrical charge depends on the pH of the buffer used for electrophoresis. If the pH exceeds the protein's isoelectric point, a negative charged protein would migrate towards the anode in the electrical field. If the pH is below the isoelectric point, the protein is likely to have a positive charge causing it to migrate towards the cathode.

A restriction endonuclease (i.e., restriction enzyme) is added to cleave a nucleic acid (e.g., DNA or RNA) at certain sites along the macromolecule. Similarly, a proteinase or protease (i.e., proteolytic enzyme) is used to break protein chains into shorter peptides or break the peptides into amino acids.

With respect to DNA, a restriction enzyme has the ability to recognize a short, specific sequence of nucleotide bases (such as, adenine, cytosine, thymine, and guanine) and severe the DNA molecule at these recognition sites by catalyzing the hydrolysis of the bond between adjacent nucleotides. Although some types of restriction enzymes are known to cleave DNA at specific sites within the recognition site; other types of restriction enzymes cleave DNA randomly, sometimes hundreds of bases from the recognition sequence.

A restriction enzyme's ability to cut DNA at precise locations is germaine to a researcher's ability to isolate gene fragments and recombine them with other DNA molecules. Understandably, precise manipulation of DNA fragments is crucial to recombinant DNA technology or genetic engineering.

It is also important to be able to accurately measure or determine the unit activity of a restriction enzyme. The unit activity (also referred to as the "unit call") is the least concentrated dilution of restriction enzyme (specifically, proteolytic enzyme for proteins) that results in a complete digestion of the macromolecule (i.e., nucleic acid or protein).

Conventionally, one may determine the unit activity by visually detecting when, for example, a DNA fragment would disappear into the background of a support matrix. Such subjective calls are prone to human error and inherent inaccuracies. As a result, the unit activity could be misjudged by a significant factor. Subjective quantitation of enzymes makes it difficult to produce consistent products and control production costs.

Another problem is related to the separation medium used to analyze DNA fragments. The separation medium may have multiple wells or lanes for apportioning the DNA samples throughout the gel. Each lane represents the result of one reaction. Adjacent lanes can be related to each other such that, as one travels from left to right, each lane represents the result of decreasing concentration of the enzyme used in each reaction to generate the visualized banding pattern seen in each lane of the gel. As the DNA fragments separate during electrophoresis, various factors (such as pH levels) can interfere with the flow in each lane. These factors can prevent each lane from running equivalently. In other words, the fragments do not migrate equivalent distances throughout the gel. This results in a wavy pattern (also known as a smile effect) that makes it difficult to align the DNA fragments across lanes and interpret the electrophoretic results.

Thus, there is a need in the art for a method and device that can accurately and objectively determine the unit activity or other catalytic results of a restriction enzyme.

SUMMARY OF THE INVENTION

The present invention is directed to a method and system for processing fragment population information that is generated from a stained macromolecule situated in a separation medium to objectively and quantitatively determine catalytic results (such as, the unit activity) of an enzyme. The term "enzyme," as used herein, is intended to include restriction enzymes, proteolytic enzymes or the like.

A test aliquot, comprising a macromolecule (such as, DNA, RNA, protein, peptide or the like) and diluted enzyme concentration, is distributed in the separation medium containing a plurality of wells. The enzyme concentration acts as a catalysis to cleave the macromolecule into distinct fragments prior to the macromolecule being distributed in the separation medium. Each well within the separation medium produces a distinct lane of electrophoretic results. Adjacent wells, and hence lanes, have relationship with one another. From left to right, each lane represents the result of decreasing concentration of the enzyme used in each reaction to generate a visualized banding pattern seen in each lane. The lane-to-lane dilution difference in enzyme concentration is the same from one lane to the next.

In an embodiment of the present invention, an intensity data profile is produced from digital images of the fragments to produce a series of stacked profiles. The stacked profiles are used to provide a model of the fragments resolved from the electrophoretic separation and residing in lanes below the reaction wells of the separation medium.

The stacked profiles are vertically aligned to designate and assign each fragment within its respective lane aligned to the identical fragment in each adjacent lane. A group of partial band(s) and final band(s) are selected from the fragments. Peak integrations are implemented to measure the intensity of the partial and final bands. A series of intensity ratios are computed from the peak integrations. The ratios embody the intensity of the specified partial band relative to the intensity of the specified final band.

After the intensity ratios have been computed and normalized, the intensity ratios are used to produce a trend approximation. A threshold crossing value is assigned a value at which the trend approximation crosses below a threshold crossing level. This unique intersection is characteristic of the enzyme strength of the original test sample.

A product-specific calibration factor is calculated by dividing the threshold crossing value by a historical unit value. The historical unit value is the industry-specified amount of restriction enzyme required to obtain complete digestion of, for example, a DNA substrate under specified assay conditions. Once the calibration factor has been calculated, the threshold crossing value is divided by the calibration factor to determine the reported unit call.

In an embodiment, a technique is provided to highlight certain data if their removal would change the results by more than one-half of a lane interval, or if data points are unusually far from the fitted model. The operator can review the highlighted points, exclude the data from analysis, and refit the model.

BRIEF DESCRIPTION OF THE FIGURES

The accompanying drawings, which are incorporated herein and form part of the specification, illustrate the present invention and, together with the description, further serve to explain the principles of the invention and to enable a person skilled in the pertinent art to make and use the invention. In the drawings, like reference numbers indicate identical or functionally similar elements. Additionally, the leftmost digit(s) of a reference number identifies the drawing in which the reference number first appears.

DETAILED DESCRIPTION OF THE PREFERRED EMBODIMENTS

Table of Contents

Figure 1:
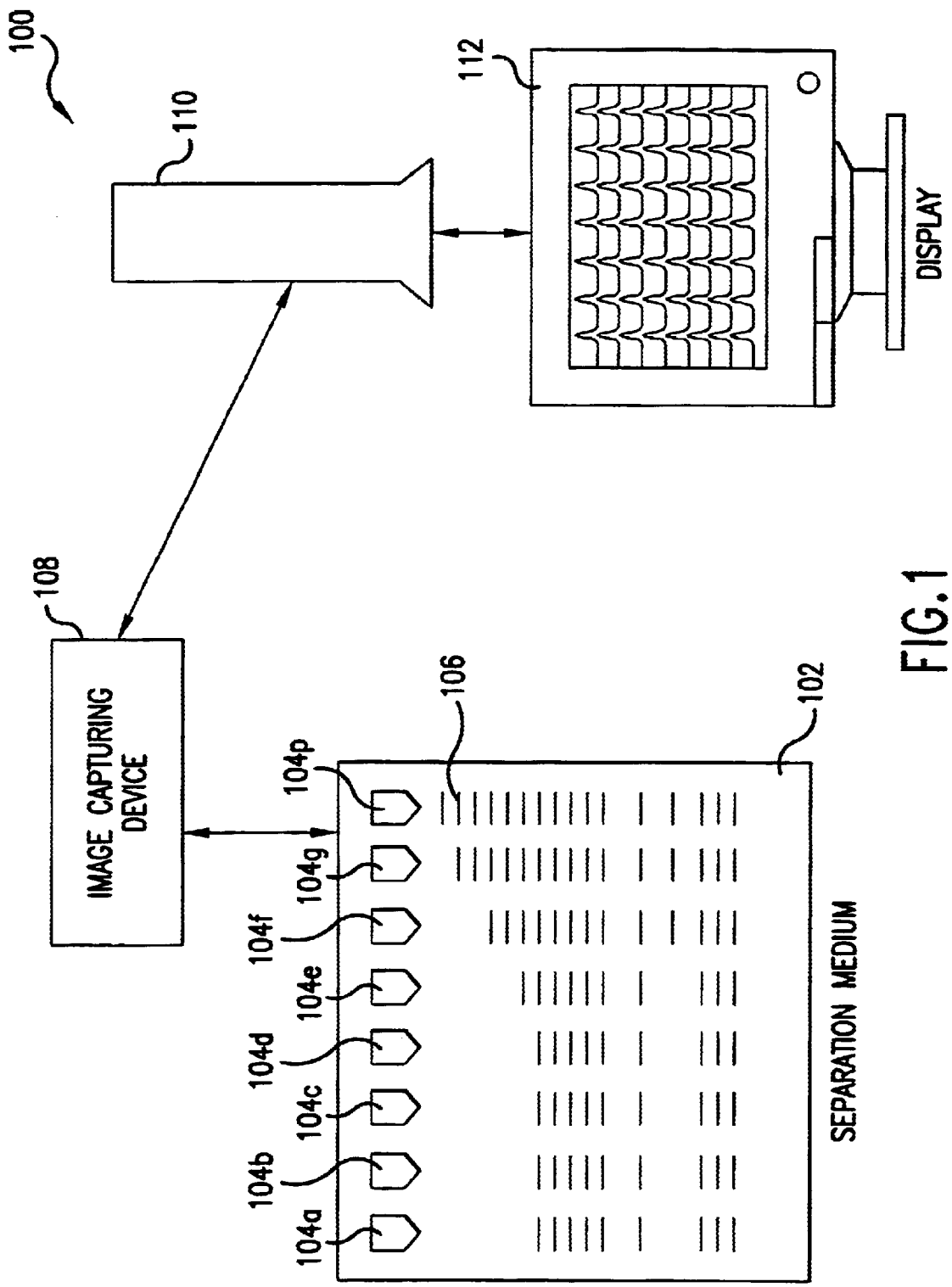
FIG. 1 illustrates a high-level block diagram of an embodiment of a electrophoretic analysis system.

I. System Overview
II. Assay Setup
III. Image Capturing
IV. Unit Activity Projection
V. Software and Hardware Embodiments
VI. Conclusion I. System Overview FIG. 1 illustrates, according to an embodiment of the present invention, system 100 for rendering objective, quantitative measurements of endonuclease activity. System 100 includes a separation medium 102, image capturing device 108, processor 110 and display 112.

Separation medium 102 utilizes electrophoretic techniques or methodologies to separate macromolecules in hydrated gels of acrylamide, agarose or the like. In an embodiment, separation medium 102 is, for example, of the type described in commonly assigned U.S. Pat. No. 5,888,364, issued Mar. 30, 1999, in the name of Michael W. Schuette, and entitled "Gel Electrophoresis Apparatus" (hereinafter referred to as "the '364 patent"). The disclosure of the '364 patent is incorporated herein by reference as though set forth in its entirety. However, the present invention should not be interpreted as being limited to the configuration of the '364 patent. Separation medium 102 can be any type of device used for electrophoresis, as would be apparent to a person skilled in the relevant art(s). In an embodiment, separation medium 102 includes Horizon™ 10–14 gel boxes available from Invitrogen Corporation (formerly, Life Technologies Inc.), and miniature external recirculation pumps (e.g., available from Cole-Parmer Instrument Company). The pumps produce a gentle flow of electrophoresis buffer over the top of the agarose gel bed. This flow prevents localized distortions in the sieving characteristics of the agarose gel bed through promotion of even resistive heat dissipation. The pumps ideally deliver a preset, even volumetric flow rate between 90 to 140 milliliters (ml) per minute. Higher flow rates tend to dislodge the agarose gel bed from the casting tray and interrupt electrophoresis operations.

Referring to FIG. 1, separation medium 102 includes a plurality of reaction wells 104a–104p. The area directly below each reaction well 104a–104p represents a lane. Samples of DNA, RNA, proteins, peptides or like macromolecules are distributed into wells 104a–104p where the samples separate upon application of an electric current through the gel according to their molecular weights. The results of the electrophoretic separations are shown as bands 106. Thus, the samples would travel down the respective lane below each reaction well 104a–104p to produce one or more bands 106 at the completion of the electrophoresis.

Image Capturing Device 108 is any type of imaging system used to measure the contrast of bands 106. The image contrast is measured as the difference in the optical properties, such as absorption, emission, or scattering characteristics, between the subject to be imaged (i.e., band 106) and its surroundings or background (i.e., the gel or mechanical structure supporting band 106). The contrast (i.e., spectral signature or intensity) of the imaged subject is measured to create an intensity profile. In an embodiment, image capturing device 108 measures luminescence (including fluorescence, phosphorescence, chemiluminescence, or the like) from the image. For example, the macromolecule samples are treated with a flourescent material that emits electromagnetic radiation towards image capturing device 108.

In an embodiment, image capturing device 108 is a Digital Science® Image Station 440CF using KDS1.0D software, available from Eastman Kodak Corporation, and includes a customized, optical quality, ground, colored-glass filter element. Images are collected with a Peltier-Cooled, Charge-Coupled camera that has at least a sixty micron individual pixel resolution. The resolution should include enough pixels to capture the image of interest, and a pixel intensity-resolution of minimally 4096 gray scale levels. In an embodiment, the filter element is the Chroma Band Pass 505–560 nanometers (nm) anti-reflective coated doublet filter or equivalent singlet (495–560 nm) available from Chroma Inc. The optical filter can be designated as either Chroma 495 to 550 or Chroma 505 to 560. In both designs, Russian Blue speciality glass is used in combination with a Shott yellow glass, where the difference in performance between the two filters is related to the relative thickness of the two glasses in combination.

In another embodiment, a dicroic filter is used. However, high quality, large objective multi-layer reflective dielectric type filters are typically expensive, difficult to source at or above a 50 millimeter (mm) objective size, and have incidence-angle dependencies that tend to reject fluorescence signals from the edge of an image. While in the preferred embodiment, image capturing device 108 includes an optical filter element, the present invention can be implemented without a custom optical filter element.

Processor 110 receives and analyzes the intensity profiles from image capturing device 108. Processor 110 represents one or more computers providing various shared resources with each other and to the other components of system 100. The shared resources include files for programs, web pages, databases and libraries; output devices, such as, printers and plotters; and communications devices, such as, modems and Internet access facilities. The communications devices can support wired or wireless communications, including satellite, terrestrial, radio, microwave or any other form or method of transmission. In an embodiment, processor 110 is configured to support the standard Internet Protocol (IP) developed to govern communications over public and private Internet backbones. The protocol is defined in Internet Standard (STD) 5, Request for Comments (RFC) 791 (Internet Architecture Board). Processor 110 can also support transport protocols, such as, Transmission Control Protocol (TCP), User Datagram Protocol (UDP) or Real Time Transport Protocol (RTP). Processor 110 is also configured to support various operating systems, such as, the Netware™ system available from Novell®; the MS-DOS® system, the Windows NT® system or the Windows® 3.xx/95/98/2000 system available from Microsoft®; the Linux® system available from Linux Online Inc.; the Solaris™ system available from Sun Microsystems, Inc.; or the like as would be apparent to one skilled in the relevant art(s).

Display 112 is a monitor or other display device that communicates with processor 110. In an embodiment, display 112 provides a text or graphical user interface (GUI) that enables a user to interactively communicate with processor 110. Display 112 can be coupled to a dumb terminal or a personal computer configured to query or respond to processor 110. In an embodiment, display 112 includes an input device that supports communications with processor 110. The input device can be a keyboard, mouse, mouse wheel, joystick, rudder pedals, touch screen, microphone, joystick, stylus, light pen, or any other type of peripheral unit. The aforementioned is a representative list of input devices that can be used with the present invention, it should be understood that any other type of input device, as would be apparent to one skilled in the relevant art(s), could be easily included and would not change the scope of the invention. Any presently available or future developed device that is responsive to a general purpose interface is encompassed by the present invention.

II. Assay Setup

Figure 2:
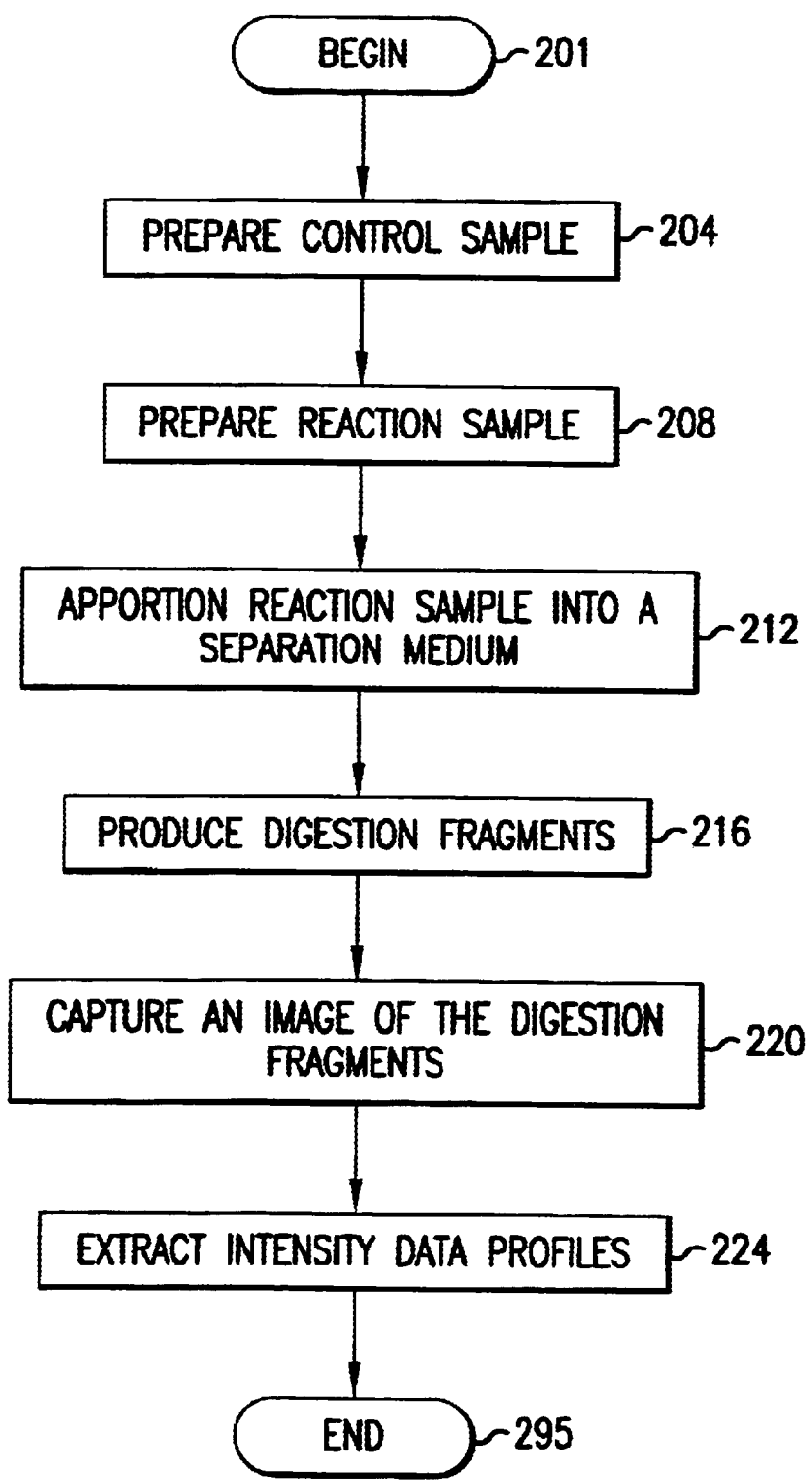
FIG. 2 illustrates on operational flow diagram for the steps involved in measuring spectral signatures of an electrophoretic sample according to an embodiment of the present invention.

Referring to FIG. 2, flowchart 200 represents the general operational flow of an embodiment of the present invention. More specifically, flowchart 200 shows an example of a control flow for producing and analyzing an image of DNA fragments, or any other combination of enzymes and substrates that can be resolved into intermediate populations and final populations. As discussed, the methods and systems of the present invention can also be used to evaluate the cleavage or formation (i.e., Gateway) of RNA, protein, peptides or other macromolecules.

The control flow of flowchart 200 begins at step 201 and passes immediately to step 204. At step 204, the operator prepares a control sample to demonstrate normal or expected endonuclease activity likely to have occurred during the course of an assay. In an embodiment, three control samples are prepared. Early, mid and late stage consistency samples are used as the control samples to provide early, mid and late-stage digestion patterns. A fourth sample of un-cut DNA substrate is also prepared. An examination of these control samples is used to detect over or under-digestion due to reagent or incubation variations. This can be accomplished by comparing the measured results from the control samples with the prescribed boundaries set for the restriction enzyme that is being assayed.

At step 208, test samples of a substrate mix (in this embodiment, DNA substrate mix) and enzyme concentration are prepared by an operator. In an embodiment, single-use aliquots of DNA substrate are combined with a 10× reaction buffer that is specified for the enzyme that is being assayed. For some enzymes (such as, EcoR II, Nde II, Rsr II or the like), a final concentration of dithiothreitol (DTT) is required to support the reaction. Hence, the DNA substrate mix would include the requisite volumes of DNA, 10× reaction buffer, DTT (if required) and distilled water.

The preparation requirements for the enzyme concentration depend on the type of assay selected. In an embodiment, two types of assays can be used to analyze and measure endonuclease activity. A wide range assay is a scouting assay initially used to estimate unit activity. If, on the other hand, the operator is highly confident in the unit activity estimate, a narrow range assay can be selected.

Figure 3:
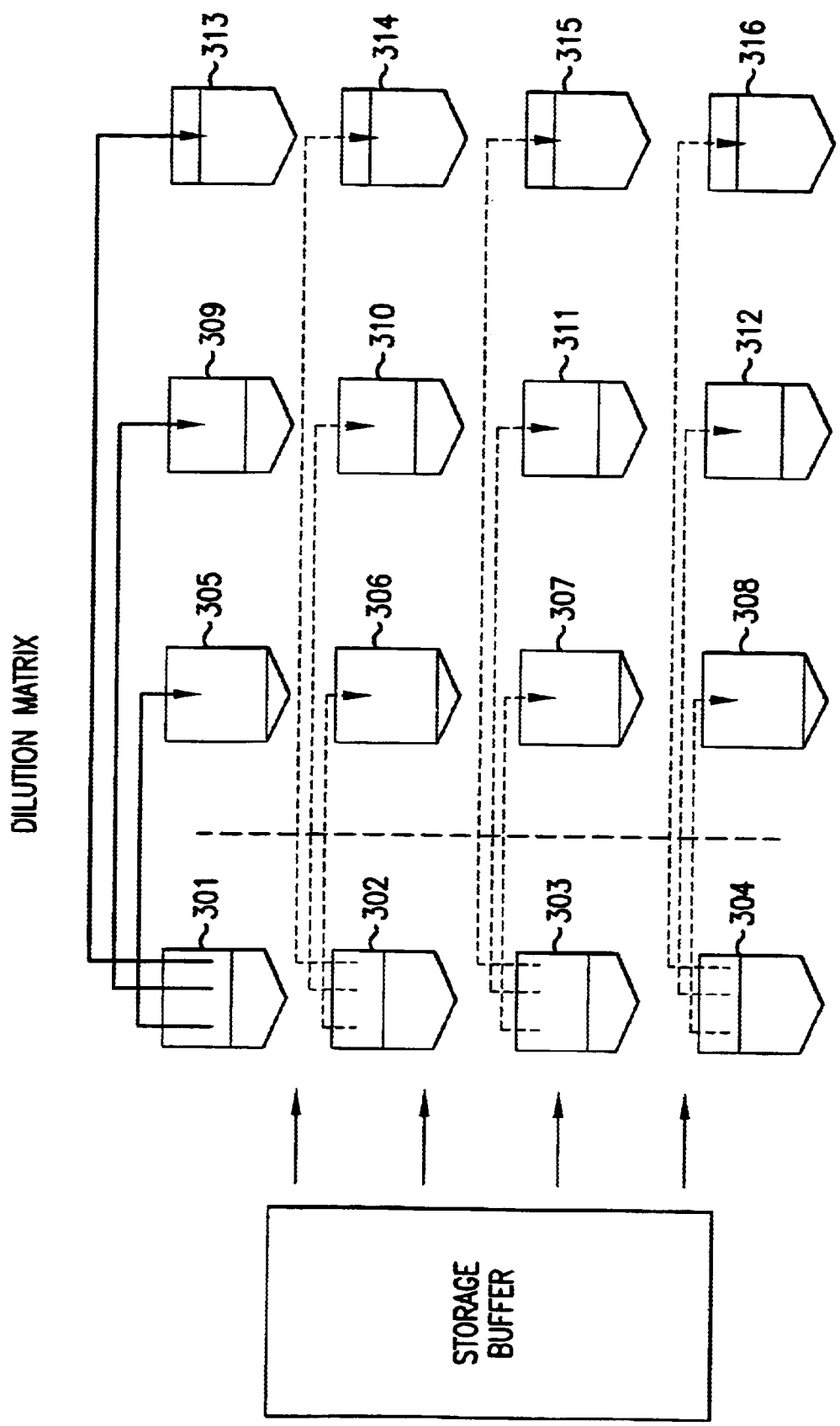
FIG. 3 illustrates a dilution matrix according to an embodiment of the present invention.

Once the assay type has been selected, an operator prepares a storage buffer and transfers the storage buffer to dilution matrix tubes, as would be apparent to one skilled in the relevant art(s). FIG. 3 illustrates a dilution matrix according to an embodiment of the present invention. FIG. 3 shows a four-by-four matrix that represents sixteen tubes used to prepare a series of test samples. Four tubes are designated as pre-dilution tubes 301–304, and twelve tubes are designated as dilution tubes 305–316. It should be noted, however, that a wide range assay of sample concentrations could have twelve pre-dilution tubes.

First, an operator calculates the volumes of storage buffer that is added to pre-dilution tubes 301–304. This is accomplished by determining a total fold (TF), which is defined as the magnitude increment dilution applied to samples across the pre-dilution series. In an embodiment, the total fold is determined by referencing Table 1 for a wide range assay or Table 2 for a narrow range assay.

TABLE 1

Wide Range Total Fold

| Estimated Activity | TF | Pre-Dilution Series |
|---|---|---|
| 2.5 to 25 units per $\mu l$ | 1 | no pre-dilution series |
| 25 to 250 units per $\mu l$ | 10 | 10 $\mu l$ into 90 $\mu l$ S.B. |
| 250 to 2,500 units per $\mu l$ | 100 | 10 $\mu l$ into 990 $\mu l$ S.B. |
| 2,500 to 25,000 units per $\mu l$ | 1,000 | 10 $\mu l$ into 90 $\mu l$, then 10 $\mu l$ into 990 $\mu l$ S.B. |

TABLE 2

Narrow Range Total Fold

| Estimated Activity | TF | Pre-Dilution Series |
|---|---|---|
| 4.7 to 47 units per $\mu l$ | 1 | no pre-dilution series |
| 47 to 470 units per $\mu l$ | 10 | 10 $\mu l$ into 90 $\mu l$ S.B. |
| 470 to 4,700 units per $\mu l$ | 100 | 10 $\mu l$ into 990 $\mu l$ S.B. |
| 4,700 to 47,000 units per $\mu l$ | 1,000 | 10 $\mu l$ into 90 $\mu l$, then 10 $\mu l$ into 990 $\mu l$ S.B. |

After the total fold has been determined, a dilution target (DT) is also determined to serve as an estimate of endonuclease activity. In other words, the operator determines a dilution target to provide an estimated guess of the dilution factor or unit activity. In an embodiment, the dilution target is determined as:

$$\text{Dilution Target} = [EA \times (TV \div SQ)] \div AM$$

where EA represents the estimated activity in units per microliter ($\mu l$); TV represents the transfer volume out of the dilution matrix shown in FIG. 3; SQ is the substrate DNA quantity per reaction well 104a–104p; and AM is the assay midpoint. The assay midpoint depends on the assay type that has been selected. For a wide range assay, the assay midpoint is determined by $1.585^{(Center\ Lane-1)}$. For example, if lane six is the center lane, the assay midpoint would be 10.00. If, however, a narrow range assay is chosen, the assay midpoint is determined by $1.19^{(Center\ Lane-1)}$. For example, if lane six is the center lane, then the assay midpoint would be 2.38. The parameters "1.585" and "1.19" are lane-to-lane dilution factors that corresponds to the type of assay selected (i.e., wide or narrow range assay).

For example, for a test sample using a wide range assay and having an estimated activity of approximately 220 units per $\mu l$, a transfer volume of 5.0 $\mu l$, an assay midpoint of 10.0 and 2.5 micrograms ($\mu g$) DNA per reaction, the dilution target would be calculated as 44 fold dilution [i.e., "[220 units per $\mu l \times (5\ \mu l \div 2.5\ \mu g\ DNA)] \div 1.585^{(6-1)}$ fold"].

After the fold and dilution target have been determined, Tables 3–4 are used to calculate the volume per pre-dilution tube 301–304. Specifically, Table 3 provides the equations for calculating the volumes for each pre-dilution tube 301–304 for a wide range assay. Table 4 provides the equations for such calculations with respect to a narrow range assay.

TABLE 3

Wide Range Volume Calculation

| Pre-Dilution Tube | Volume |
|---|---|
| 301 | $\{[(DT \div TF) \times 1.585^0] - 1\} \times 30\ \mu l$ |
| 302 | $\{[(DT \div TF) \times 1.585^1] - 1\} \times 10\ \mu l$ |
| 303 | $\{[(DT \div TF) \times 1.585^2] - 1\} \times 10\ \mu l$ |
| 304 | $\{[(DT \div TF) \times 1.585^3] - 1\} \times 10\ \mu l$ |

TABLE 4

Narrow Range Volume Calculation

| Pre-Dilution Tube | Volume |
|---|---|
| 301 | $\{[(DT \div TF) \times 1.19^0] - 1\} \times 30\ \mu l$ |
| 302 | $\{[(DT \div TF) \times 1.19^1] - 1\} \times 10\ \mu l$ |
| 303 | $\{[(DT \div TF) \times 1.19^2] - 1\} \times 10\ \mu l$ |
| 304 | $\{[(DT \div TF) \times 1.19^3] - 1\} \times 10\ \mu l$ |

After the storage buffer has been loaded into pre-dilution tubes 301–304, the storage buffer is transferred to dilution tubes 305–316. If a wide range assay has been selected, 53 microliters of the storage buffer are loaded into dilution tubes 305–308, 388 $\mu l$ are loaded into dilution tubes 309–312; and 2,504 $\mu l$ are loaded into dilution tube 313–316. If, however, a narrow range assay has been selected, 20 $\mu l$ are loaded into dilution tubes 305–308, 60 $\mu l$ are loaded into dilution tubes 309–312; and 141 $\mu l$ are loaded into dilution tubes 313–316.

After the storage buffer has been distributed, the operator prepares the initial four dilutions of the restriction enzyme test sample and distributes the test sample into pre-dilution tubes 301–304. The amount transferred depends on the assay type that has been selected. For a wide range assay, 30 $\mu l$ of the test sample are transferred to tube 301; and 10 $\mu l$ are transferred to each of the tubes 302–304. For a narrow range assay, 20 $\mu l$ are transferred to tube 301; 15 $\mu l$ are transferred to each of tubes 302–303; and 10 $\mu l$ are transferred to tube 304.

After the restriction enzyme test sample has been distributed among pre-dilution tubes 301–304, the operator prepares dilution tubes 305–316 for multiple non-serial dilutions. The amount distributed depends on the assay type. For wide range assays, 10 $\mu l$ are transferred from tube 301 to dilution tubes 305, 309 and 313; 10 $\mu l$ are transferred from tube 302 to dilution tubes 306, 310 and 314; 10 $\mu l$ are transferred from tube 303 to dilution matrix tubes 307, 311 and 315; and 10 $\mu l$ are transferred from tube 304 to dilution tubes 308, 312 and 316. For narrow range assays, 20 $\mu l$ are transferred from tube 301 to dilution tubes 305, 309 and 313; 20 $\mu l$ are transferred from tube 302 to dilution tubes 306, 310 and 314; 20 $\mu l$ are transferred from tube 303 to dilution tubes 307, 311 and 315; and 20 $\mu l$ are transferred from tube 304 to dilution tubes 308, 312 and 316.

Each pre-dilution tube 301–304 and dilution tube 305–316 has a corresponding reaction tube (not shown). Likewise, each control sample (i.e., early, mid and late-stage consistency samples and an un-cut DNA substrate) has a corresponding control tube (not shown). An operator loads each reaction tube (not shown) and control tube (not shown) with 120 $\mu l$ of DNA substrate mix. The reaction tubes are placed in a water bath set for a controlled temperature. The operator also initiates the reactions one at a time by removing each reaction tube (not shown) from the water bath to load the reaction tube with 5 $\mu l$ of enzyme concentration from a corresponding pre-dilution tube 301–304 and dilution tube 305–316. Similarly, the operator loads each control tube (not shown) with a corresponding control sample. As each reaction is initiated, the operator returns the reaction tube (not shown) to the water bath set at the controlled temperature for a specified incubation time period. At the end of the specified incubation period, the reactions are stopped in the same order as they have been initiated. When the reactions are stopped, the restriction enzyme has cleaved the DNA substrate into various fragments of digestion.

Referring back to FIG. 2, after test samples of the DNA substrate mix and diluted enzyme concentration are prepared at step 208, the control flow passes to step 212 where test aliquots of the solution are distributed to reaction wells 104a-104p of separation medium 102 for electrophoresis. The test aliquots are distributed by apportioning the DNA substrate mix (including the appropriate reaction buffers and diluted enzyme samples) from the reaction tubes (not shown) to corresponding reaction wells 104a–104p. The control samples are likewise transferred to a designated control well.

It should be noted, however, that in an embodiment, the control samples are provided for visual analysis and comparison. The control samples are used to detect, but not quantify, significant errors related to a final digestion reaction. Thus, the control samples are used to develop a confidence level that a reported value, as determined below, is valid. In another embodiment, the same enzyme concentration is run as a control sample. In this embodiment, reaction wells 104a-104p are modified to include 20 lanes. As values are generated, as discussed below, processor 110 warns the operator if the values are outside an expected range.

Figure 4:
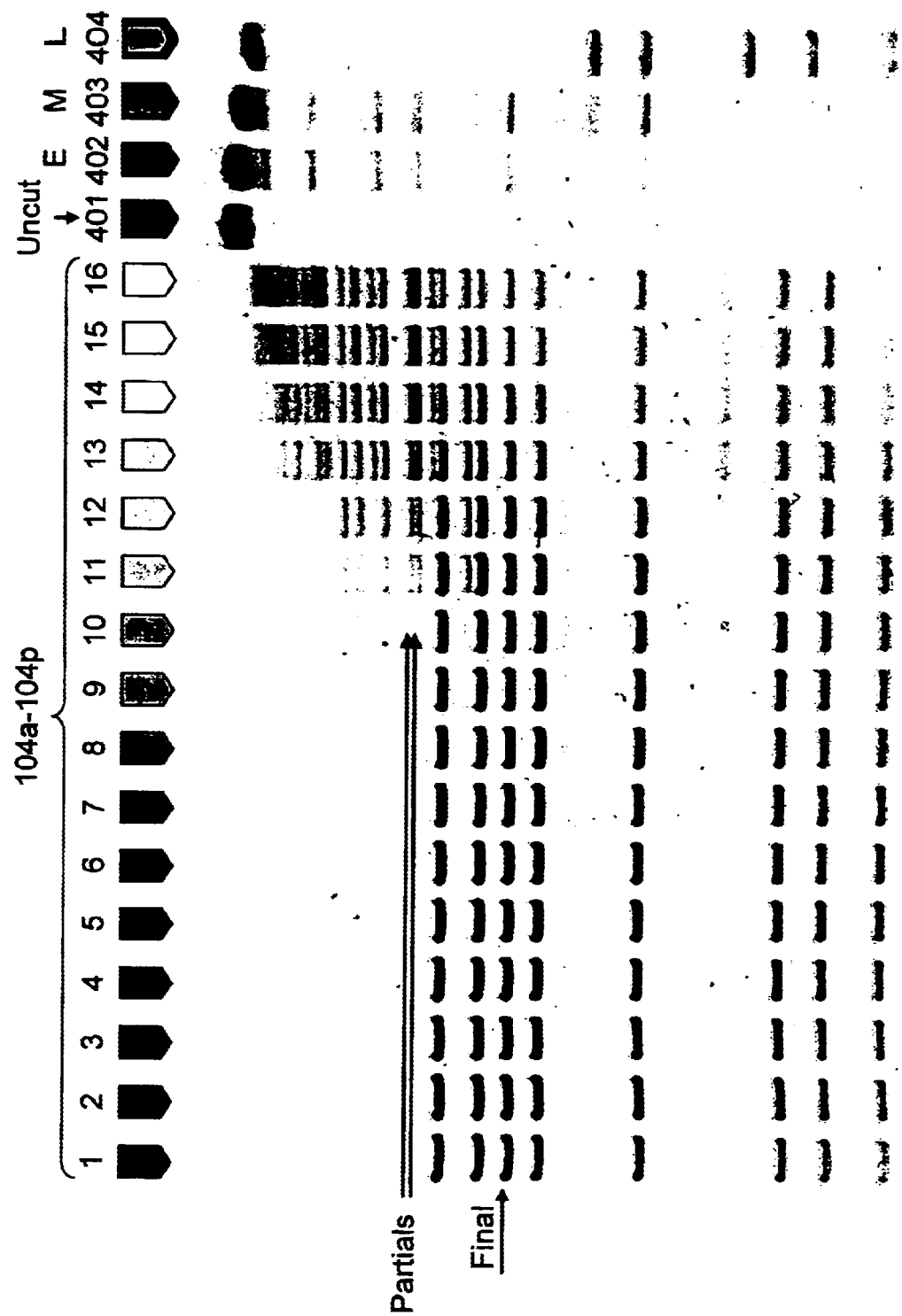
FIG. 4 illustrates reaction and control wells from the separation medium shown in FIG. 1, according to an embodiment of the present invention.

FIG. 4 illustrates an embodiment of separation medium 102 that includes sixteen reaction wells 104a–104p and four control wells 401–404. Reaction wells 104a–104p are used to resolve the DNA samples. The four control wells 401–404 are used to evaluate the un-cut DNA substrate and the early, mid and late-stage digestion patterns, as discussed above.

Referring back to FIG. 2, at step 216, the gel is run to initiate the electrophoresis in reaction wells 104a–104p and control wells 401–404. In this embodiment, an agarose gel is used to separate the DNA sample. To improve resolution for the subsequent imaging process (discussed below), the volume of the gel should be 60 milliliters (ml), and the amount of buffer solution in the electrophoresis apparatus should be 850 ml.

Referring back to FIG. 4, separation medium 102 shows the DNA substrate fragments as they line up according to molecular weight in the respective lane located below the respective reaction wells 104a–104p. Likewise, fragments from the control samples also line up below the respective control wells 401–404. The conditions for separating the DNA substrate fragments should be optimized to obtain optimally straight and narrow final banding patterns to avoid a wavy pattern or smile effect that often occurs in gel electrophoresis. Nonetheless, as discussed below, the methods and system of the present invention are designed to overcome the problems due to waviness.

III. Image Capturing

Referring again to FIG. 2, in step 220, the operator uses image capturing device 108 to produce an image of the DNA fragments residing in the lanes below reaction wells 104a–104p of separation medium 102. Prior to capturing the gel images in an embodiment, the resolved DNA fragments are stained with a reporter molecule, such as the SYBR® or SYPRO® fluorescent reagents available from Molecular Probes, Inc., including without limitation SYBR® Gold, SYBR® Green, SYPRO® Ruby, and the like. The SYBR® Gold flourescent reagent, for example, has high fluorescence yield on binding, and does not require de-staining prior to being imaged. Other fluorescent regents, such as ethidium bromide, can be used. However, ethidium bromide must be de-stained to reduce the fluorescent from interfering with the subsequent intensity measurements from the gel images. For quantitation of proteins, similar use of a fluorescent stain such as the SYPRO® fluorescent reagents (e.g., SYPRO® Ruby) available from Molecular Probes, Inc. can be used to detect and quantify the relative concentrations of each protein fragment after electrophoretic resolution. A non-fluorescent absorption-mode stain such as Commassie Blue R-250 can also be used to detect and quantify a protein fragment, but would require destaining.

Following the staining and de-staining (if required) process, high spatial (approximately 0.1 mm) and intensity resolution (i.e., 12 bit minimum) gel images are collected. As discussed, in an embodiment, the images are obtained using SYBR® Gold staining with data collected by a Digital Science® Image Station 440CF running KDS1.0D software available from Eastman Kodak Corporation. The Image Station 440CF is capable of digitizing the images at one-minute intervals until a maximum signal greater than 4,000 is reached. To improve the reliability of the subsequent intensity measurements, the images should be free of visual artifacts, such as, large smears, gel tears, strong row curvature (e.g., waviness patterns), fading of bands toward one side of gel, or extreme band deformation.

As described above in reference to FIG. 1 in an embodiment, image capturing device 108 includes a custom optical filter element that is configured to improve the raw signal quality of the image. For SYBR® dye-fluorescence signal quantitation, the filter should be designed to reject short wavelength excitation wavelengths below 470 nm entirely as well as longer wavelengths above 550 nm. The filters should be able to substantially transmit SYBR® dye emitted fluorescence between 495 nm to 530 nm, irrespective of angle of incidence, and without introduction of optical distortion. If another reporter molecule is used, the optical filter must be adjusted to match the excitation and emission characteristics of that particular dye.

As discussed, a fluorescent stain such as SYPRO® Ruby, or a non-fluorescent absorption-mode stain such as Commassie Blue R-250 can be used to quantify the concentration of a protein fragment after electrophoretic resolution. The filter system would be adjusted to the properties of each of these dyes as specified by the respective manufacturer.

At step 224, image capturing device 108 processes the images to extract the intensity data profile for each lane of DNA fragments. The profile includes a set of horizontally summed pixels scanned from top to bottom within a lane. In an embodiment, image capturing device 108 uses Digital Science® 1D Image Analysis Software Version 3.0. available from Eastman Kodak Corporation to obtain the intensity data profiles. The software scans each lane on the gel images to determine the intensity measurements. It should be understood that any combination of molecular reporter, and hardware and software capable of digitizing fragment size distributions with comparable fidelity would be consistent with the data analysis and extraction operations of the present invention. After the intensity data profiles have been extracted, the control flow ends as indicated by step 295.

IV. Unit Activity Projection

Figure 5:
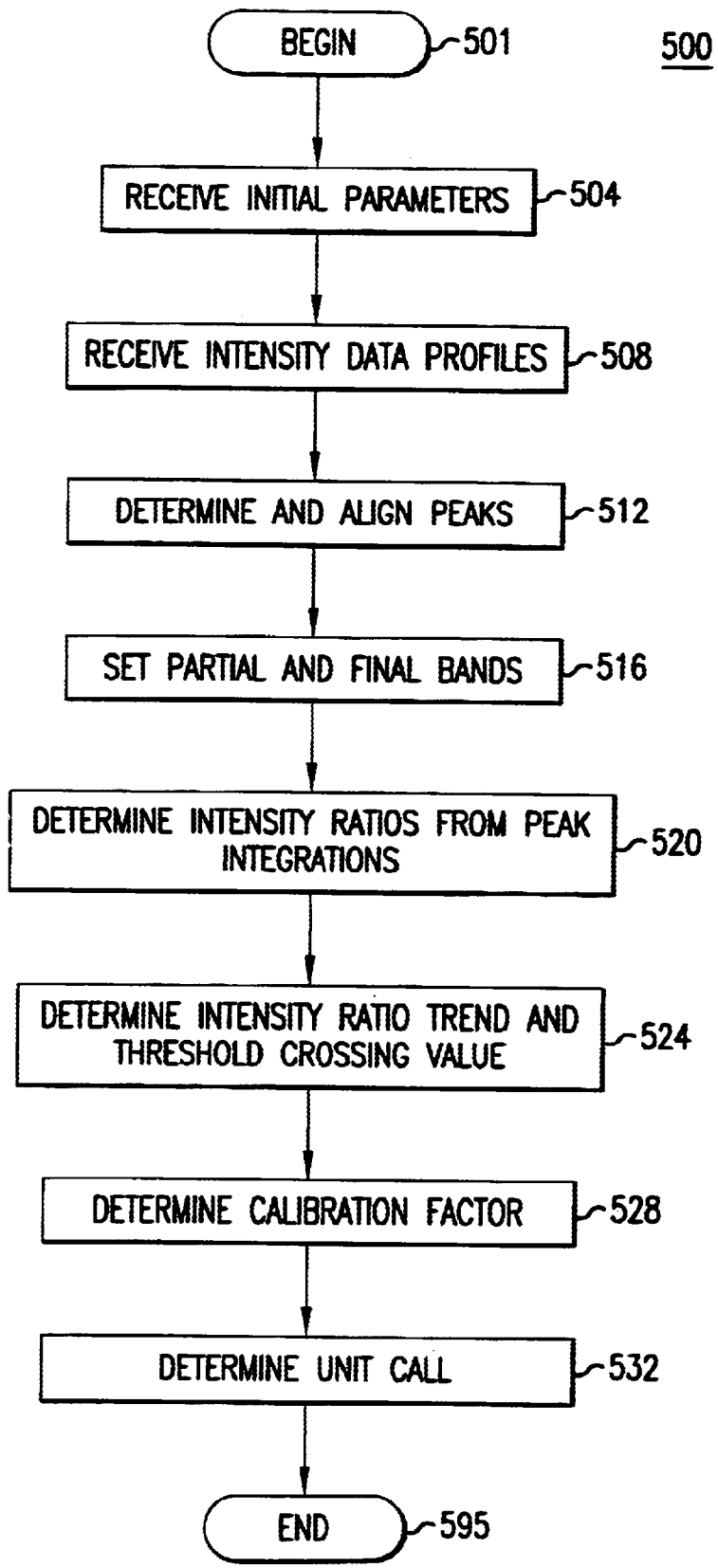
FIG. 5 illustrates an operational flow diagram for the steps involved in determining unit activity according to an embodiment of the present invention.

FIG. 5 illustrates a general operational flow of an embodiment of the present invention. More specifically, flowchart 500 shows an example of a process for analyzing an image of bands of partial and full DNA fragments to quantify endonuclease activity. In an embodiment, a Microsoft® Excel worksheet is used to quantify the activity. However, other data processing software or programming languages can be used to implement the methods of the present invention, as would be apparent to one skilled in the relevant art(s).

FIG. 5 begins at step 501 and passes immediately to step 504, where the requisite initial parameters are entered by the operator or loaded from a storage medium for use during subsequent calculations. The parameters include various threshold values used to analyze unit activity, a molecular weight ratio, a calibration factor, or the like, as discussed in detail below.

Additionally at step 504, the operator enters, or system 100 loads, a lane-to-lane dilution factor which corresponds to the type of assay selected (i.e., wide or narrow range assay). For a wide range assay, the lane-to-lane dilution factor is 1.585, and for a narrow range assay, the lane-to-lane dilution factor is 1.19.

Another parameter loaded or entered at step 504 is a dilution target. As described in reference to step 208 in FIG. 2, the dilution factor is based on the lane-to-lane dilution factor for the selected assay type. The dilution target serves as an estimate of endonuclease activity. However in combination, the dilution target and the lane-to-lane dilution factor uniquely and completely describe a set of physical dilutions created by manipulating a sample through a dilution matrix, such as the dilution matrix illustrated in FIG. 3. Thus, these parameters enable processor 110 to properly interpret a raw image profile set to determine the amount of dilution applied to the samples that generated the distinct banding pattern for each lane profile.

Processor 110 would use the dilution target and lane-to-lane dilution factor to produce an estimated guess of unit activity by calculating an effective dilution target representing 66–75% complete digestion. First, a lane-specific physical dilution factor is calculated as:

$$\text{Physical Dilution Factor (Lane)} = (DT \times LL^{(Lane-1)}) \times (TV/SQ)$$

where "Lane" identifies the specific lane number; and DT, LL, TV and SQ are the values discussed in reference to step 208 for the dilution target, lane-to-lane dilution factor; transfer volume, and substrate DNA quantity, respectively. The physical dilution factor must be adjusted to account for the volume of reaction mixture containing the DNA substrate. In an embodiment, 5 $\mu$l of sample is transferred into 120 $\mu$l of reaction mixture containing 2.5 $\mu$g DNA substrate. Based on empirical observations, the physical dilution factor in this embodiment must be reduced by a factor to two to produce a more accurate measure of the test sample unit strength. As such, the lane-specific effective dilution factor is calculated as:

$$\text{Effective Dilution Factor (Lane)} = \text{Physical Dilution Factor (Lane)} \div 2$$

where the value "2" is the unit strength adjustment factor. As would be apparent to one skilled in the relevant art(s), the unit strength adjustment factor would vary according to the reaction volume, substrate quantity, transfer volume or the like. As such, effective dilution factors representing 66–75% completion are calculated to derive a projection of a unit call (herein referred to as a "reported unit call") representing complete digestion as per unit definition.

Referring back to step 504, another parameter loaded or entered is a threshold crossing level. The threshold crossing level is assigned a value where the bands of DNA fragments continue to provide a strong, robust intensity signal, but is set sufficiently above background noise levels to assure an accurate signal quantitation. For instance, for a narrow range assay, the threshold crossing should be between the second and third intensity data points that still have a clear signal. However, the threshold crossing for a narrow range assay can be set at any point above an area having at least two noise data points above the background noise level, or having at least two data points above a region where the operator has a high degree of confidence.

Also, entered or loaded at step 504 is a historical unit assay value for the restriction endonuclease that is based on empirical observations, industry standards or vendor specifications. In short, the historical unit assay value states the restriction enzyme unit definitions at which point customers can expect to attain complete digestion of substrate DNA under a set of prescribed conditions. In an embodiment, the historical unit assay value represents the amount of enzyme required to digest 1 $\mu$g of the appropriate substrate DNA completely in sixty minutes under the conditions specified for the enzyme.

At step 508, the intensity data profiles are received from a memory source or image directory. The intensity data profiles can be retrieved from an input file stored in a temporary or permanent memory location on a hard disk drive or removable storage device, such as a floppy diskette, magnetic tape, optical disks, or the like, and loaded into processor 110. In addition to the intensity data, the input file would identify the type of enzyme that has been assayed. An output file can also be created to store relevant test results, as described below in further detail.

At step 512, processor 110 reads the intensity measurements (e.g., pixel values) from the intensity data profiles into a data structure for further processing. As discussed, each intensity data profile represents chromatographic data derived from a distinct lane within the digital image that is produced from image capturing device 108. In an embodiment, processor 110 adjusts or corrects the intensity data profiles to remove background intensity and/or scattering effects. This process helps to reduce any interference caused by the fluorescent reagent or the gel support matrix used to stain the DNA fragments. In an embodiment, the correction process is implemented by subtracting an offset from each pixel. The offset corresponds roughly to the background fluorescence and excitation source scattered breakthrough. The offset is computationally equivalent to the lowest pixel in each intensity data profile.

The background corrected intensity data profiles are copied to a second data structure. With the second data structure, processor 110 inserts linearly interpolated points between each raw data point in the original set of intensity data profiles. Processor 110 uses this technique to mitigate any problems arising from the DNA bands not being straight or the DNA bands producing a wavy pattern in the digital image.

Upon completion of the point-by-point linear insertions, peaks are detected within each set of pixel data from the modified intensity data profiles. In other words, each lane (as represented by a respective intensity data profile) would contain one or more peaks that signal higher levels of intensity measurements. Each peak represents, for example, a DNA substrate fragment (i.e., DNA band).

In an embodiment, processor 110 traces the pixels point-by-point to detect the peaks. A state-engine based derivative tracking system is used to detect the changes in trace direction that occur at peaks and troughs in a pixel data set. The state-engine is governed by logical limitations that prevent frivolous response to tiny fluctuations in the pixel data set. The first limit is based on hysteresis or minimum change. This limit is set as a fraction of the maximum pixel intensity within a given intensity data profile. Therefore, the limit adjusts to intensity variations from one intensity data profile to the next.

The second logical limitation is a peak rejection interval which is a predetermined number of pixel data points. This limitation is based on an assumption that the peaks of interest will be spaced no closer than a certain number of pixel data points. Therefore, the state-engine would reject peaks or troughs that occur at intervals more closely spaced than the peak rejection interval. This limitation is empirically determined based on the resolution of image capturing device 108, zoom optics, and quality of the electrophoretic separation. In an embodiment, the peak rejection interval is set to two pixel data points.

Once a listing of peaks is obtained for each intensity data profile, the peaks are sorted and aligned to determine the peaks that most likely correspond to each other from profile to profile (i.e., referring to the captured image, from lane to lane). This allows the DNA bands to be correctly associated with the proper lane (i.e., from the sixteen reaction wells 104*a*–104*p*). This is implemented by processor 110 selecting an intensity data profile (and, hence, a lane), and matching the peaks in the selected profile with the most likely associated peaks in the other profiles.

This is performed as a three step process. Processor 110 would select the intensity data profile corresponding with, for example, lane 10. Based on empirical data, the lane-to-lane band pixel offsets in high-quality images rarely exceed plus or minus seven full pixels. Thus, in the first step, a list of pixel positions in lane 10 is compared to the pixel positions in lane 9. A scanning process locates the closest peaks in lane 9 within seven pixels of each peak in lane 10. If one peak in lane 9 is assigned to two or more peaks in lane 10, the assigned peaks are scanned for consistency relative to other neighboring peak offsets, and one peak is chosen. The other peaks are de-assigned.

The process continues comparing lane 9 to lane 8, lane 8 to lane 7, and so forth until lane 1 is processed. A similar process compares lane 10 with lane 11, lane 11 to lane 12, and so forth until lane 16 is encountered.

Upon completion, processor 110 establishes a table to associate each peak to a neighboring lane. The differences are calculated and also stored in the table as peak offset values. The peak offset values are scanned for image-wide relationships. During this process, processor 110 searches for peak systems that continue as far as possible from lane 10 to lane 1 and to lane 16. Those peaks that form complete mountain-line ranges of associated peaks are identified and copied to a third data structure.

The offsets between neighboring peaks are refined by application of an iterative comparison process. For each lane, a set of nine pixels having a centered peak pixel is compared to a set of similar sets of nine pixels from a flanking lane centered about the peak offset values discussed above. This is implemented by using fractional pixel steps made possible from the continuous linearly interpolated values derived from the original intensity data profiles. During the iterative comparison, processor 110 calculates the summed square difference between the nine pixels from each lane. Each multiple pixel sum square difference is compared to the previous best sum with lower values considered to be closer matches between the two lanes snippets. The fractional offset that yields the lowest score is taken to be the refined offset between two peaks, and is stored in the data structure associated with that pair of peaks. This process continues down each lane and across from lane 10 to lane 1 and lane 10 to lane 16. For each peak in each lane, an integrated refined offset is then calculated by tracing along the association path. This value is stored in a data table associated with the peak itself.

The integrated refined offsets are taken to be guideposts in an intensity data profile that indicate points of equivalence among multiple intensity data profiles. A function is defined to return the intensity of pixels in a lane in terms of a reference frame based on the pixels in lane 10. In other words if one requests a corrected pixel 27 in lane 4, the computation calculates the actual position in lane 4 that would correspond to pixel 27 in lane 10. This calculation includes a routine that expands and/or contracts segments of any given lane other than lane 10. This is accomplished by linear interpolation in a piecewise fashion where the peaks in lane 4 corresponding to peaks flanking pixel 27 in lane 10 are used as guideposts and indeed endpoints for the interpolation process. For each pixel within this flanking region, an offset is calculated as the linearly interpolated value of the offset at the endpoints and the returned actual pixel position in lane 4 (which is likely fractional) is returned. This actual pixel position corresponding to pixel 27 in lane 10 is retrieved from the lane 4 data set with fractional values returned by linear interpolation in all cases. Thus, the expansion/contraction is accomplished through use of associated refined guidepost peak positions to generate linearly interpolated offset indexes that are used as direct fractional-pixel queries into the original linearly interpolated data set through the lens of the defined expansion/contraction function.

In an embodiment, no accommodation is made for an apparent gain or loss of original signal intensity that occurs on expansion and contraction. It has been observed that the correction methodologies or techniques of the present invention generally are consistent in a local sense and lead to minute discrepancies. To increase the accuracy in intensity integration, the returned pixel intensity for a given location is adjusted by a degree of compression at that pixel. This is defined as the change in offset from an upper to a lower guidepost peak divided by the number of pixels between the peaks in the original peak data set and would be a number very close to unity in most cases.

To present an aligned set of pixels, processor 110 scans through the data sets for each lane using the expansion/contraction function and displays the data as lists using the charting functions of a graphics application, such as the Microsoft® Excel application available from Microsoft Corporation (Redmond, Wash.). The display is created in half pixel increments for clarity and presentation purposes. The profiles are given a fixed offset for display only that allows them to be displayed one on top of the next thus making the trends in the data set intuitive and easy to see.

Figure 6:
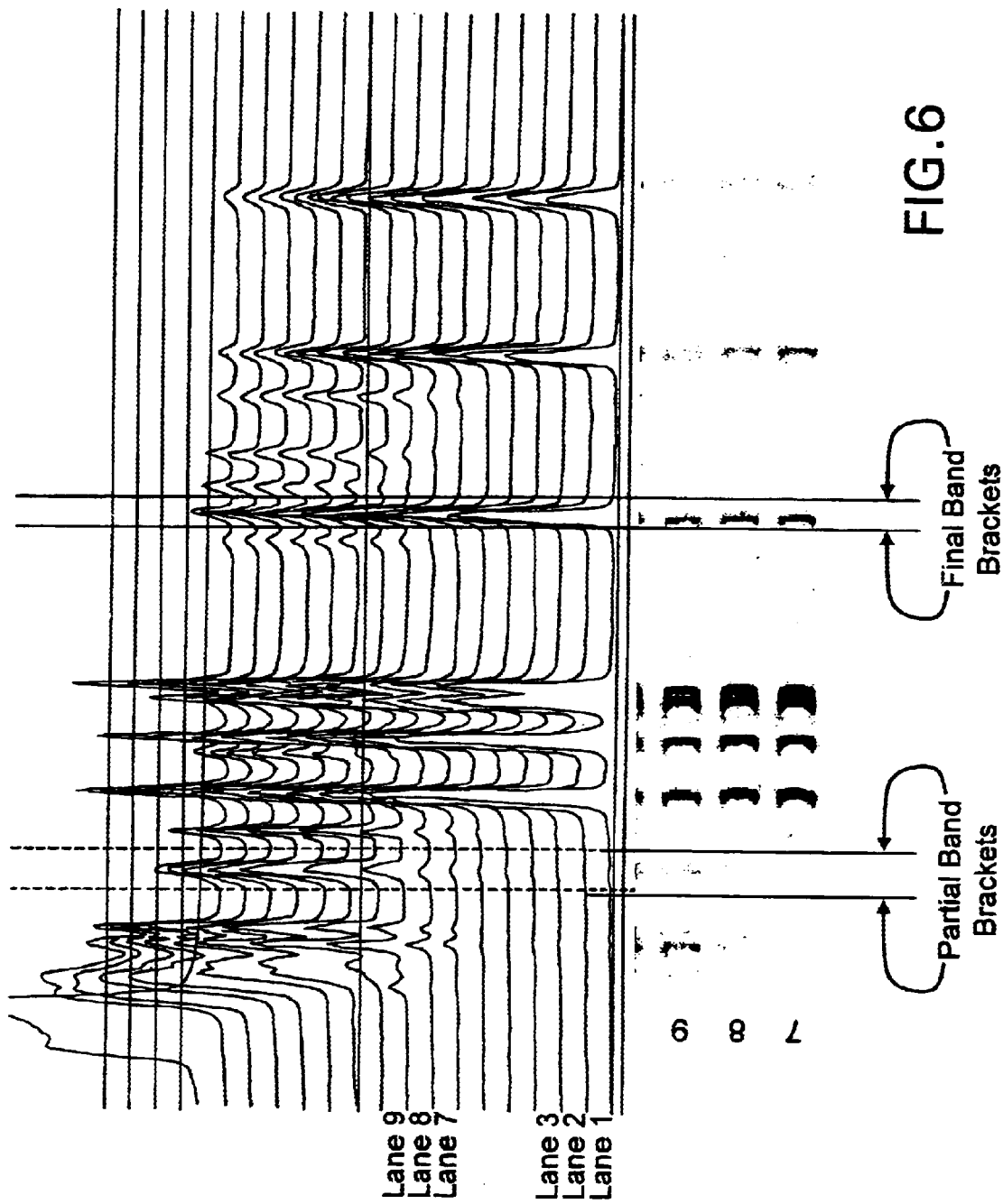
FIG. 6 illustrates a stacked profile display according to an embodiment of the present invention.

FIG. 6 shows this series of stacked lane profiles that are displayed on display 112. As can be seen, the peaks from the profiles are vertically aligned. In other words, the related DNA bands (represented by the peaks) in the stacked lane profiles share the same region along the horizontal axis of a graph.

Referring back to FIG. 5, at step 516, a set of partial and final DNA bands are selected for analysis. In an embodiment, processor 110 selects the partial and final bands based on preset criteria. In another embodiment, the operator designates the locations of these two bands of interest by using an input device (e.g., mouse) to position graphical brackets on either side of the desired peaked-stacked sets. Referring again to FIG. 6, the peaks or DNA bands selected as the partial bands are designated with a dotted bracket, and the peaks or DNA bands selected for the final bands are designated with a solid bracket. The edges of the brackets define the background for the peak measurements.

Accordingly, the operator positions brackets around a pre-defined set of peaks which must include one or more partial band peak associations and one or more final band associations. The bracket positions are used to define initial limits of integration for each peak within associated peak sets. To be more specific, the initial limits of integration for each peak are refined iteratively by scanning two pixels on either side of both the lower and upper initial limits searching for the refined limits that return the largest integrated sum. The reason for this final refinement is seated in both relieving the operator of finding an exactly optimum bracket position and in allowing for any small residual alignment drift that may be present across the full 16 lane span of the data set. The resulting integrated peak intensities for the partial and final bands are stored.

Referring back to FIG. 5, at step 520, processor 110 evaluates the bracketed regions to extract a set of intensity ratios. Each intensity ratio relates the intensity value of the partial band to the intensity value of the final band. The intensity values for the bands are computed from the local background corrected integrated peak intensities from bracketed regions. Accordingly, an intensity ratio is computed for each lane from the gel image. The calculated intensity ratios are estimates of the extent to which the DNA substrate has been digested by the enzyme concentration in each reaction well 104a–104p.

Since the intensity of a DNA band is proportionally related to its molecular weight, the intensities ratios can also be normalized by taking the product of the integrated intensity values and the inverse of their respective molecular weights, or:

$$\text{Normal Intensity Ratio} = [(I_p/I_f) \times (MW_f/MW_p)]$$

where $I_p$ and $MW_p$ represent the integrated intensity value and molecular weight, respectively, for a partial band, and $I_f$ and $MW_f$ represent the integrated intensity value and molecular weight for a final band.

During the peak integrations described to compute the intensity ratios, processor 110 is operable to adjust or correct the intensity data profiles by removing outliers or other faulty data. In an embodiment, processor 110 highlights intensity data points with a "1" to signal questionable data points. The "1" indicates the reported unit activity is strongly influenced by the associated data point.

In an embodiment, a data point is highlighted with a "1" if its exclusion changes the result by more than 25% for a wide range assay, or by more than 10% for a narrow range assay. Processor 110 also highlights data points with a "2" if they are judged to be located at an unusual distance from a predetermined range but does not change the final unit result. Type-2 highlights draw attention to minor potential anomalies in the intensity data profile that when properly reviewed can lead to an improvement in result certainty. The operator can choose to exclude the type-1 or type-2 data points by changing the designation to a "0." Once the data point is excluded, processor 110 refits the intensity data to the model.

Again, an empirical assumption is made for the final process of the data. That assumption is that the normalized band intensity ratio should decrease monotonically in the region where the unit value for the enzyme concentration had been historically assigned. That is, one must know that based on statistical modeling of the restriction reaction, it is not physically feasible to predict an abrupt increase in the normalized band intensity ratio with decreasing sample dilution. However, such abrupt increases are from time to time noted in practice. These abrupt increases are attributable to physical limitations of the experimental implementation including pipette inaccuracy, operator error, and simple mixing problems. In fact, the degree to which a series of normalized band intensity ratios smoothly define a transition is a strong indication of validity in the final result. This observation is a matter of intrinsic design for the present invention starting with the use of an interleaved, expanded tube number dilution matrix having equally tempered geometric lane-to-lane dilution spacing.

A unique, robust and efficient method has been developed to take advantage of these observations. The method is based on finding the lowest score configuration of a multi-parameter coupled-body mathematical model. Each body is initially placed on top of each point on the raw normalized band intensity ratios plotted on a double logarithmic chart versus the effective dilution factors. A higher score is assigned to a body if the change in the vector direction from that body to its neighbors differs from the same change of those neighbors. That is, lower scores are assigned to smoothly curving configurations of points. This is referred to as the curvature strain. The sum of these squared curvature changes is calculated. A similar sum is made of the two-dimensional square differences for each of the bodies from the original data set points. The curvature strain term is weighted and summed with the distance sum. This forms the score of any given coupled body configuration.

An optimization model is constructed to find the most optimal configuration of the coupled bodies based on minimizing the above score function. The optimization model executes an implementation of non-linear optimization, so that each intensity axis value is changed by the optimization model for the coupled-bodies until the smallest score is obtained. In an embodiment, the optimization model is based on the Excel Solver function from the Microsoft® Excel application available from Microsoft Corporation. However, other software applications can be built or used as would be apparent to one skilled in the relevant art(s).

At step 524, the normalized intensity ratios are used to determine a threshold crossing value. Generally, the normalized intensity ratios approach lower limits as the dosage of enzyme yields complete digestion of the DNA substrate. When a calculated trend from these intensity ratios approaches a threshold crossing level, the corresponding threshold crossing value provides a measure of dilution. The threshold crossing level is one of the initial parameters entered at step 504.

The intensity ratio trend is calculated from the final configuration of coupled-bodies from the optimization model. The final configuration represents the very-likely reaction trajectory described by the underlying raw normalized band intensity ratio values. Thus, processor 110 produces a linearly-interpolated line which is calculated to connect these bodies. The intersection of this line with a line set at the threshold crossing level defines the threshold crossing value (in terms of effective dilution factor). If a data point is located far away from the final coupled body configuration, the data point is highlighted, as described above, as a possible point in error for further operator review.

Figure 7:
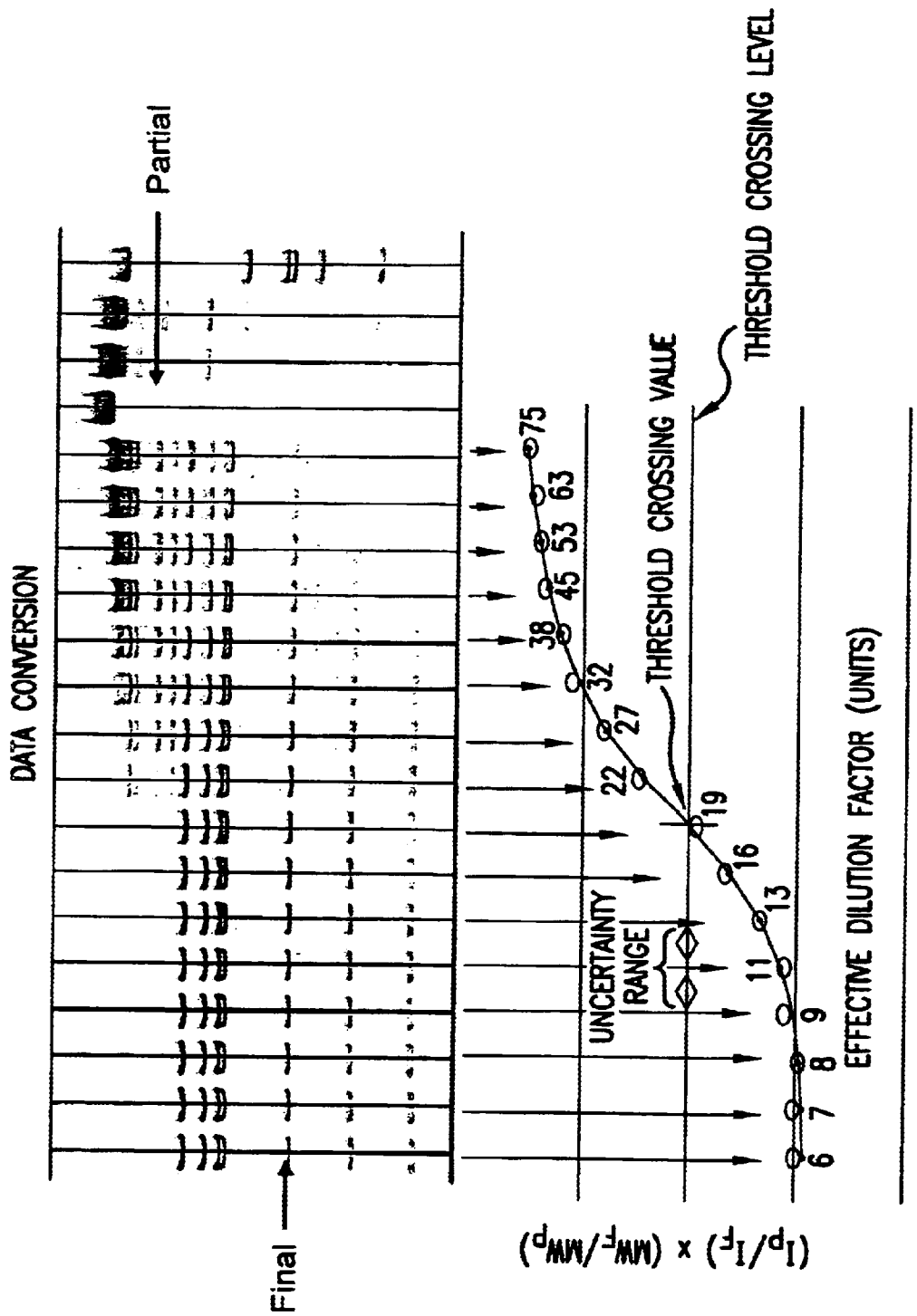
FIG. 7 illustrates a partial profile display according to an embodiment of the present invention.

FIG. 7 illustrates a partial profile display according to an embodiment of the present invention. FIG. 7 shows a trend produced from a set of intensity ratios. The trend is plotted on a log scale of intensity ratios versus effective dilution factors. In this example, the threshold crossing level, from step 504, is designated as 0.01. As discussed, the threshold crossing level is selected at a point above the noise region, but where a strong, robust intensity signal can be quantified. The trend approaches the threshold crossing level at a point designated as the threshold crossing value. In this example, the threshold crossing value is approximately "18.9."

After the trend has been approximated and the threshold crossing value has been computed, the control flow passes to step 528. At step 528, a calibration factor is computed from the threshold crossing value. As discussed, the threshold crossing value is a derived value dependent on effective dilution factors, and an effective dilution factor does not represent the complete digestion of the DNA substrate. Rather, the effective dilution factor is a measure of a partial digestion of the DNA substrate at some point prior to its complete digestion, usually between 66 to 75% complete.

To calculate the calibration factor, the threshold crossing value is divided by the historical unit assay value entered at step 504 above. The historical unit assay value is used to convert the threshold crossing value into a historically expected unit by assay of enzyme products having well accepted historical unit strengths. Once the calibration factor has been established under known, controlled conditions, the calibration factor is fixed and remains unchanged during assay of unknown samples.

At step 532, the reported unit value is calculated by dividing the threshold crossing value by the calibration factor from step 528. Accordingly, the calibration factor is used to roughly calibrate the system and method of the present invention with unit activity measurements that are historically accepted by the restriction endonuclease industry. As a result, the present invention maximizes product consistency. Moreover, the methods and systems of the present invention allow unit activity to be determined objectively from intensity measurements. The reported unit call is an objective estimation of reaction completion that is not based on conventional methods of visually detecting the vanishing of band signal intensity.

In an embodiment, partial-to-final band ratios, threshold crossing values, unit calls, other results and/or other context information are stored in an output file or a database (not shown) for historical reference. Additionally, in an embodiment, the range of certainty in the reported result(s) is also computationally estimated using a Monte-Carlo technique. Thirty permutations of the sixteen data point x and y axis in the original data set are created. The permutations are created using normally distributed random numbers centered around zero and having standard deviations based on known inaccuracies in the assay design. For each of these thirty permutations, the resulting unit values are obtained and stored. Finally, a standard deviation calculation is applied to the unit values to obtain an estimate of the stability of the raw data set configuration.

A similar sort of operation is also applied to sixteen further permutations of the raw data set through point-by-point deletion. Again, a standard deviation calculation is applied to the resulting list of unit values. Together, the statistically combined standard deviations are combined, multiplied by two, and reported as the range of error for the originally reported unit value. Processor 110 would also set a flag for further operator review for any raw data point whose removal would causes a change of greater than a certain limit in the reported unit value. This prevents the present invention from reporting unit values that are supersensitive to a single data point.

V. Software and Hardware Embodiments

As is apparent from the foregoing description, the present invention was developed primarily to measure enzyme unit activity for digesting a DNA, RNA, protein or peptide substrate. However, it would be clear to persons skilled in the relevant art(s) that the analysis techniques of the present invention have utility beyond the endonuclease activity described above. The invention has application outside this area and can be used generally to analyze and measure any type of titrations or biochemical activities.

The present invention (e.g., system 100, image capturing device 108, processor 110, display 112, or any part thereof) can be implemented using hardware, software or a combination thereof and can be implemented in one or more computer systems or other processing systems. In fact, in an embodiment, the invention is directed toward one or more computer systems capable of carrying out the functionality described herein.

Figure 8:
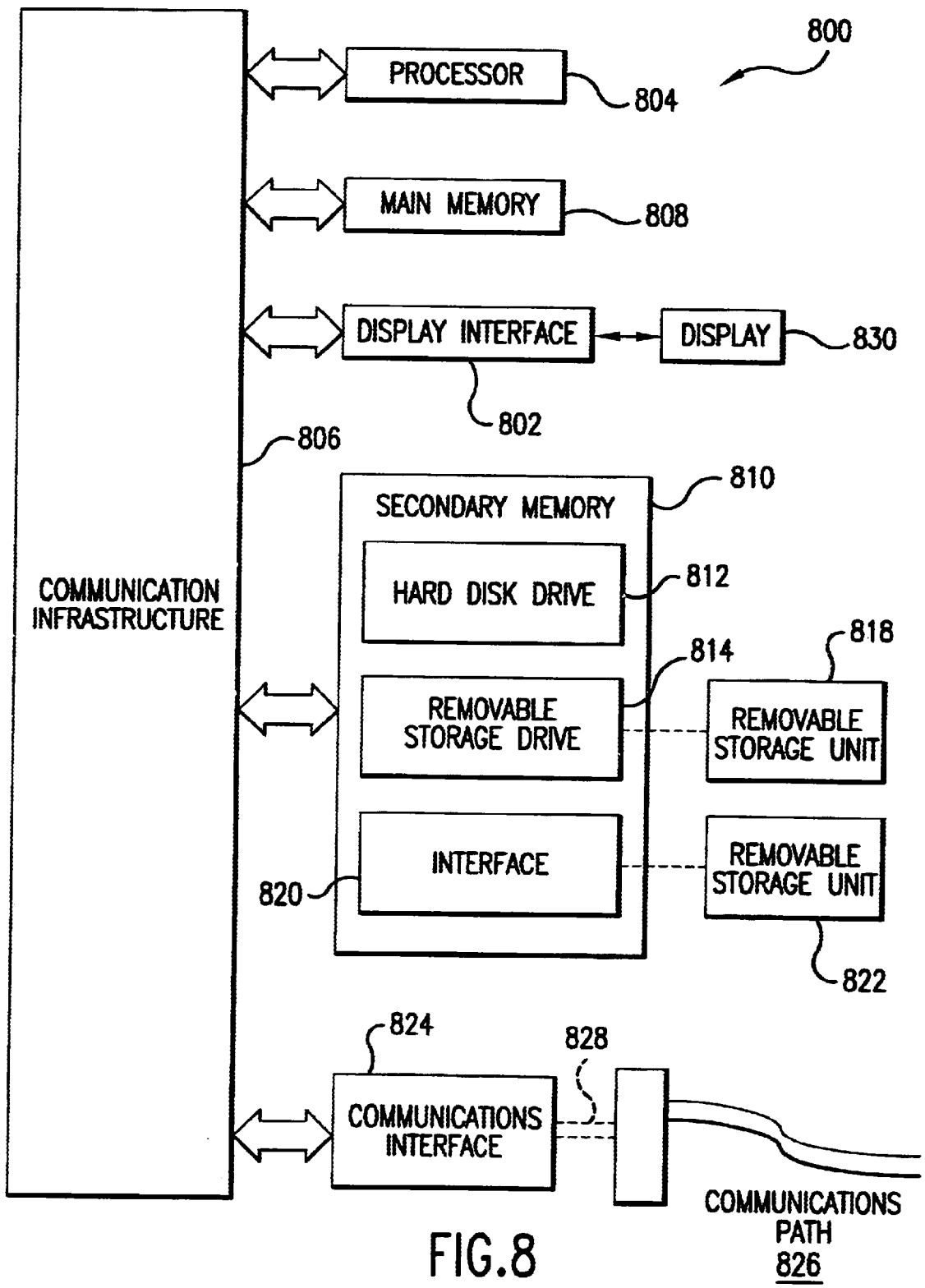
FIG. 8 illustrates is a block diagram of an example computer system useful for implementing the present invention

Referring to FIG. 8, an example computer system 800 useful in implementing the present invention is shown. The computer system 800 includes one or more processors, such as processor 804. The processor 804 is connected to a communication infrastructure 806 (e.g., a communications bus, cross-over bar, or network). Various software embodiments are described in terms of this exemplary computer system. After reading this description, it will become apparent to a person skilled in the relevant art(s) how to implement the invention using other computer systems and/or computer architectures.

Computer system 800 can include a display interface 802 that forwards graphics, text, and other data from the communication infrastructure 806 (or from a frame buffer not shown) for display on the display unit 830.

Computer system 800 also includes a main memory 808, preferably random access memory (RAM), and can also include a secondary memory 810. The secondary memory 810 can include, for example, a hard disk drive 812 and/or a removable storage drive 814, representing a floppy disk drive, a magnetic tape drive, an optical disk drive, etc. The removable storage drive 814 reads from and/or writes to a removable storage unit 818 in a well-known manner. Removable storage unit 818, represents a floppy disk, magnetic tape, optical disk, etc. which is read by and written to removable storage drive 814. As will be appreciated, the removable storage unit 818 includes a computer usable storage medium having stored therein computer software and/or data.

In alternative embodiments, secondary memory 810 can include other similar means for allowing computer programs or other instructions to be loaded into computer system 800. Such means can include, for example, a removable storage unit 822 and an interface 820. Examples of such can include a program cartridge and cartridge interface (such as that found in video game devices), a removable memory chip (such as an EPROM, or PROM) and associated socket, and other removable storage units 822 and interfaces 820 which allow software and data to be transferred from the removable storage unit 822 to computer system 800.

Computer system 800 can also include a communications interface 824. Communications interface 824 allows software and data to be transferred between computer system 800 and external devices. Examples of communications interface 824 can include a modem, a network interface (such as an Ethernet card), a communications port, a PCMCIA slot and card, etc. Software and data transferred via communications interface 824 are in the form of signals 828 which can be electronic, electromagnetic, optical or other signals capable of being received by communications interface 824. These signals 828 are provided to communications interface 824 via a communications path (i.e., channel) 826. This channel 826 carries signals 828 and can be implemented using wire or cable, fiber optics, a phone line, a cellular phone link, an RF link and other communications channels.

In this document, the terms "computer program medium" and "computer usable medium" are used to generally refer to media such as removable storage drive 814, a hard disk installed in hard disk drive 812, and signals 828. These computer program products are means for providing software to computer system 800. The invention is directed to such computer program products.

Computer programs (also called computer control logic) are stored in main memory 808 and/or secondary memory 810. Computer programs can also be received via communications interface 824. Such computer programs, when executed, enable the computer system 800 to perform the features of the present invention as discussed herein. In particular, the computer programs, when executed, enable the processor 804 to perform the features of the present invention. Accordingly, such computer programs represent controllers of the computer system 800.

In an embodiment where the invention is implemented using software, the software can be stored in a computer program product and loaded into computer system 800 using removable storage drive 814, hard drive 812 or communications interface 824. The control logic (software), when executed by the processor 804, causes the processor 804 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

VI. Conclusion

While various embodiments of the present invention have been described above, it should be understood that they have been presented by way of example, and not limitation. It will be apparent to persons skilled in the relevant art(s) that various changes in form and detail can be made therein without departing from the spirit and scope of the invention. Thus, the present invention should not be limited by any of the above described exemplary embodiments, but should be defined only in accordance with the following claims and their equivalents.

What is claimed is:

1. A method for measuring catalytic activity of a test aliquot, comprising the steps of:

distributing the test aliquot into a separation medium, wherein the test aliquot includes a plurality of macromolecular fragments resulting from the catalytic activity;

enabling said plurality of fragments to separate within said separation medium;

digitizing an image of said plurality of fragments to measure intensity values from said image;

processing said intensity values to derive a fragment population model of said plurality of fragments; and analyzing said fragment population model to determine a catalytic result.

2. A method according to claim 1, wherein said distributing step comprises the step of:

distributing the test aliquot among a plurality of reaction wells within said separation medium, wherein said processing step comprises placing said intensity values into intensity profiles, each intensity profile representing a subset of said fragments from a corresponding reaction well.

3. A method according to claim 2, further comprising the steps of:

removing an intensity value lying outside of a prescribed range; and refitting said intensity profiles in response to said removing step.

4. A method according to claim 1, further comprising the step of:

calculating intensity ratios, wherein each intensity ratio is derived from an intensity value from each of two specified fragments, wherein said intensity ratios are used to determine said catalytic result.

5. A method according to claim 1, further comprising the step of:

deriving an effective dilution factor, said effective dilution factor providing a basis for analyzing said fragment population model to determine said catalytic result.

6. A method according to claim 1, further comprising the step of:

determining a unit call for said catalytic result.

7. A method according to claim 6, further comprising the step of:

determining a calibration factor for adjusting said catalytic result used to determine said unit call.

8. A method according to claim 1, further comprising the step of:

staining said plurality of fragments on said separation medium with a reporter molecule prior to said digitizing an image step.

9. A method according to claim 8, wherein said plurality of fragments are not de-stained prior to said digitizing an image step.

10. A method according to claim 1, wherein said macromolecular fragments comprise at least one of DNA fragments and RNA fragments, and wherein said enabling step comprises the step of:

performing electrophoretic separation to resolve said at least one of DNA fragments and RNA fragments.

11. A method according to claim 1, further comprising the step of:

transferring a diluted enzyme concentration to one or more reaction chambers to generate said plurality of macromolecular fragments.

12. A method according to claim 11, wherein aid diluted enzyme concentration is produced by the steps of:

apportioning a buffer solution among a dilution matrix having multiple pre-dilution tubes and multiple dilution tubes;

depositing an enzyme sample into said pry-dilution tubes to produce an enzyme concentration; and transferring portions of said enzyme concentration from said pre-dilution tubes to said dilution tubes to produce said diluted enzyme concentration.

* * * * *